US00PP18453P3

(12) United States Plant Patent
Danziger

(10) Patent No.: US PP18,453 P3
(45) Date of Patent: Jan. 22, 2008

(54) ***CHRYSANTHEMUM* PLANT NAMED 'DANAT214'**

(50) Latin Name: *Chrysanthemum morifolium*
Varietal Denomination: Danat214

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/202,054

(22) Filed: Aug. 12, 2005

(65) Prior Publication Data

US 2006/0195958 P1 Aug. 31, 2006

(30) Foreign Application Priority Data

Feb. 25, 2005 (CO) ..... A05890

(51) Int. Cl.
*A01H 5/00* (2006.01)

(52) U.S. Cl. ..... Plt./295

(58) Field of Classification Search ..... Plt./295
See application file for complete search history.

(56) References Cited

U.S. PATENT DOCUMENTS

PP15,045 P3 * 7/2004 Danziger ..... Plt./294

OTHER PUBLICATIONS

Broertjes et al. A mutant of a mutant of a mutant . . . Irradiation of progressive radiation–induced mutants in a mutation–breeding programme with *Chrysanthemum Morifolium*. Euphytica 29(1980) 525–530.*

* cited by examiner

*Primary Examiner*—Kent Bell
*Assistant Examiner*—Annette H Para
(74) *Attorney, Agent, or Firm*—Foley & Lardner LLP

(57) ABSTRACT

A new and distinct *Chrysanthemum* plant named 'Danat2l4' characterized by having inflorescence with oblong shaped, yellow ray florets, and bell shaped, yellow disc florets; flowering time of 7.5 weeks; short day plant; and vigorous growth habit.

2 Drawing Sheets

Botanical designation: *Chrysanthemum morifolium.*
Variety denomination: 'Danat214'.

BACKGROUND OF THE INVENTION

The present invention relates to a new and distinct cultivar of *Chrysanthemum* plant, botanically known as *Chrysanthemum morifolium,* hereinafter referred to by the cultivar name 'Danat214'.

The new cultivar 'Danat214' is a product of a planned mutant selection and monitoring program in Moshav Mishmar Hashiva, Israel, with the objective of finding color mutants of the *Chrysanthemum morifolium* cultivar 'Danchryat'.

The new cultivar 'Danat214' originated from induced mutation on a single flowering plant of the *Chrysanthemum morifolium* cultivar 'Danchryat' (patented, U.S. Plant Pat. No. 15,045), and grown in a controlled, cultivated environment in Moshav Mishmar Hashiva, Israel. The parental cultivar 'Danchryat' is also known by the commercial variety name Atlantis.

The new cultivar 'Danat214' was discovered and selected by the inventor, Gabriel Danziger, as an induced whole plant mutation of 'Danchryat' in January of 2003 in Moshav Mishmar Hashiva, Israel. The mutation arose by radiation.

Asexual reproduction of the new cultivar by stem cutting was first performed in January of 2004 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Danat214' which in combination distinguish this *Chrysanthemum* as a new and distinct cultivar:

1. Oblong shaped, yellow ray florets, and bell shaped, yellow disk florets;
2. Flowering time of 7.5 weeks;
3. Short day plant; and
4. Vigorous growth habit.

Plants of the new cultivar 'Danat214' differ from plants of the parental cultivar 'Danchryat' as described in Table 1.

TABLE 1

| Characteristic | 'Danat214' | 'Danchryat' (patented, PP15,045) |
|---|---|---|
| Inflorescence Diameter | 9.5 cm. | 9.5 cm. |
| Flowering Time | 7.5 weeks | 7.5 weeks |
| Growth Potency | Medium-High | Medium-High |
| Ray Floret Color | Yellow, RHS 6-B | White, RHS 155-D |
| Disk Floret Color (when opening) | Yellow-green, RHS N144-A | Yellow-green, RHS 146-B |

Of the many commercial cultivars known to the present inventor, the most similar in comparison to 'Danat214' is the parental cultivar 'Danchryat' as described in Table 1.

BRIEF DESCRIPTION OF THE DRAWINGS

The accompanying photographs illustrate the overall appearance of the new *Chrysanthemum* cultivar 'Danat214' showing the colors as true as is reasonably possible with colored reproductions of this type. Colors in the photographs may differ slightly from the color values cited in the detailed botanical description, which accurately describe the colors of 'Danat214'.

DETAILED BOTANICAL DESCRIPTION

Figure 1:
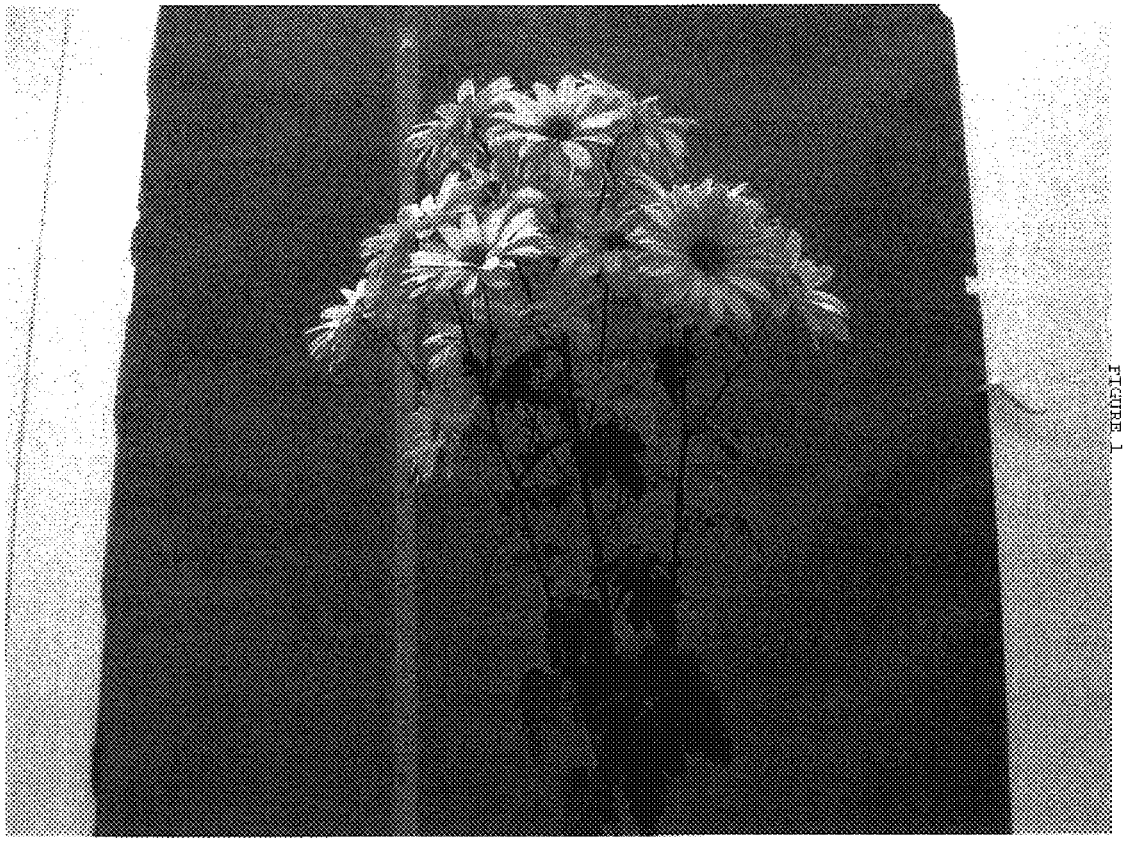
FIG. 1 shows a side view perspective of a corymb of 'Danat214'.
Figure 2:
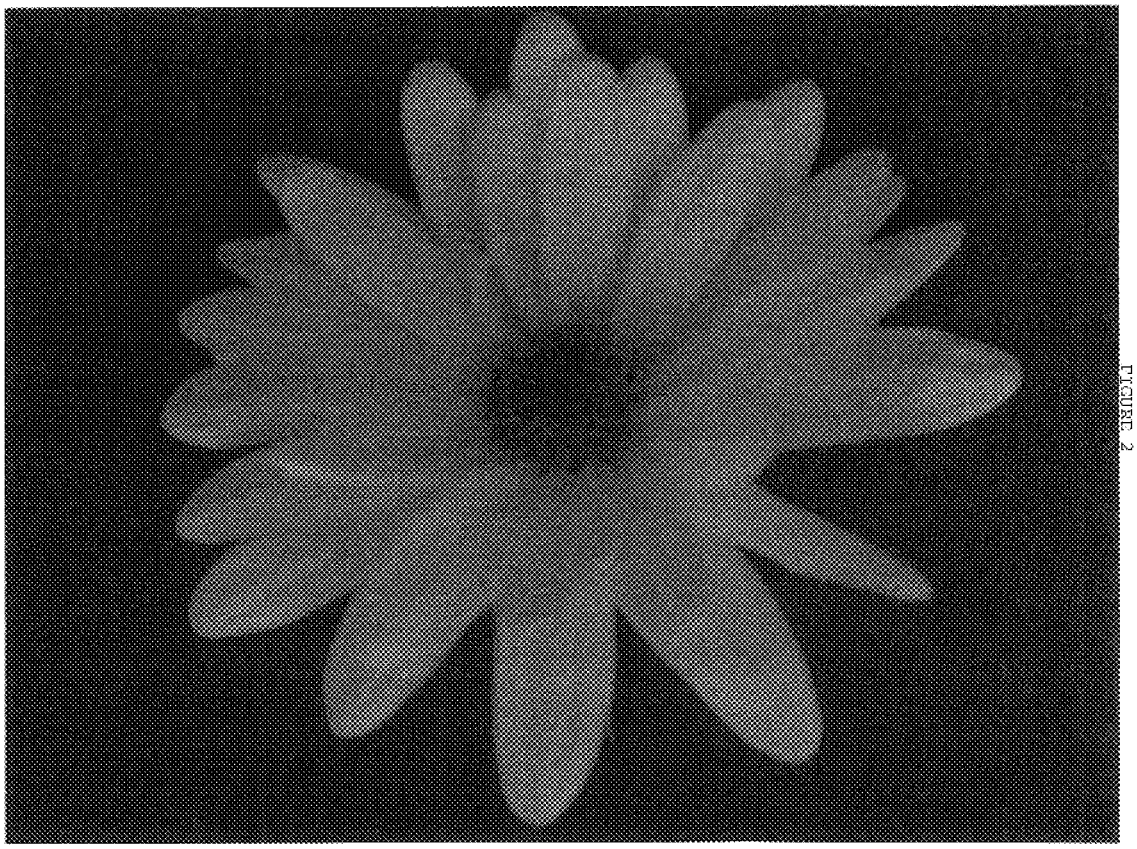
FIG. 2 shows a close-up view of an inflorescence of 'Danat214'.

'Danat214' has not been observed under all possible environmental conditions. The phenotype of the new cultivar may vary with variations in environment such as temperature, light intensity, and daylength without any change in the genotype of the plant.

The aforementioned photographs, together with the following observations, measurements and values describe the new cultivar 'Danat214' as grown in a greenhouse (confirmed) in Moshav Mishmar Hashiva, Israel, under conditions which closely approximate those generally used in commercial practice. Plants of 'Danat214' are mainly grown in greenhouses, but can also be grown outdoors during the summer. The recommended temperature range for growing plants of 'Danat214' in a greenhouse are: day temperature range of 22° C. to 23° C., and evening temperature range of 17° C. to 18° C. For premium growth conditions, plants of 'Danat214' are irrigated and fertilized on a regular basis using moderate regim. Plants of 'Danat214' are treated with the growth retardant, Alar (B-Nine), at a concentration of 3 gr/L.

Color references are made to The Royal Horticultural Society Colour Chart (R.H.S.), ed. 2001, except where general colors of ordinary significance are used. Color values were taken under daylight conditions at approximately 12:00 noon in Moshav Mishmar Hashiva, Israel. The age of the plant described is 11 weeks from planting.

Classification:

*Botanical.*—*Chrysanthemum morifolium.*

*Commercial.*—*Chrysanthemum* cv. 'Atlantis Yellow'.

Parentage:

*Parental cultivar.*—Induced mutation of *Chrysanthemum morifolium* cultivar 'Danchryat' (patented, U.S. Plant Pat. No. 15,045).

Propagation: Stem cutting.

Plant:

*General appearance and form.*—Height: 90 cm. Width: 20 cm. Shape: Compound corymbiform.

*Flowering response.*—Short day type.

*Flowering season.*—Autumn and beginning of winter.

*Winter hardiness.*—Hardy in moderate climate.

*Lastingness of the individual bloom.*—3 to 3.5 weeks (on stem).

*Rooting habit.*—Adventitious roots from cutting base.

*Time to initiate roots.*—6 to 7 days.

*Fragrance.*—None.

Foliage:

*Leaf length.*—10 cm.

*Leaf width.*—5.5 cm.

*Overall shape of leaf.*—Pinnatipartite.

*Apex shape.*—Rounded.

*Base shape.*—Wedge-shaped.

*Margin.*—Serrate.

*Texture.*—Slightly warty.

*Color of upper surface.*—Mature leaf: Yellow-green, RHS 147-A. Immature leaf: Yellow-green, RHS 147-A.

*Color of lower surface.*—Mature leaf: Yellow-green, RHS 147-B. Immature leaf: Yellow-green, RHS 147-B.

*Venation.*—Pattern: Pinnate. Upper surface: Yellow-green, RHS 147-B. Lower surface: Yellow-green, RHS 147-C.

*Petiole.*—Length: 2 cm. Diameter: 4 mm. Color: Yellow-green, RHS 146-A.

*Stem.*—Average length: 85 to 90 cm. Average diameter: 8 to 10 mm. Color: Yellow-green, RHS 146-B. Internode length: 15 to 20 mm.

Inflorescence:

*Flowering response.*—Short day.

*Quantity of inflorescences on average.*—7 to 8 on average per stem.

*Inflorescence bud.*—Height: 1 cm. Diameter: 16 mm. Color: Yellow-green, RHS 146-B.

*Inflorescence size.*—Diameter: 9.5 cm. Depth (height): 18 to 20 mm. Diameter of disc: 18 mm.

*Ray florets.*—Number of ray florets per inflorescence: 30 to 32. Orientation: Upward. Length: 35 to 40 mm. Width: 12 to 13 mm. Apex width: 4 to 8 mm. Overall shape: Oblong. Apex shape: Rounded (obtuse). Base shape: Fused. Margin: Entire. Texture: Smooth. Color when opening: Yellow group, RHS 6-B. Color when fully opened: Upper surface: Yellow group, RHS 6-B. Lower surface: Yellow group, RHS 5-C.

*Disc florets.*—Number of disc florets per inflorescence: 200 to 220. Length: 4 to 5 mm. Width: 1 mm. Overall shape: Bell-shaped (campanulate). Apex shape: Toothed. Base shape: Fused. Margin: Entire. Texture: Smooth. Color when opening: Yellow-green, RHS N144-A. Color when fully opened: Upper surface: Yellow, RHS 9-A. Lower surface: Yellow, RHS 9-C.

*Phyllaries.*—Average number: 15 to 18. Average length: 6 to 9 mm. Average width: 1 to 2 mm. Overall shape: Oblong. Apex shape: Rounded (obtuse). Base shape: Truncate. Margin: Entire. Color: Upper surface: Yellow-green, RHS 148-B. Lower surface: Yellow green, RHS 144-A.

*Peduncles.*—Aspect: Upward. Length: 15 cm. Diameter: 3.5 to 4 mm. Texture: Slightly warty. Color: Yellow-green, RHS 146-B.

Reproductive organs:

*Androecium.*—Present in disc florets only. Stamen: Number: 5, fused as a tube. Length: 5 mm. Color: Yellow, RHS 13-A. Anthers: Color: Yellow, RHS 13-A. Pollen: Color: Yellow, RHS 13-A.

*Gynoecium.*—Present in both ray and disc florets. Style: Length: 5 to 6 mm. Color: Yellow, RHS 2-B. Stigma: Width: 0.3 mm. Color: Yellow, RHS 12-B. Ovary: Color: Yellow-green, RHS 149-D. Seeds: Length: 1.5 mm. Width: 0.8 to 1 mm. Shape: Oblong. Color: Grayed-green, RHS 197-A. Fruit: Shape: Achene. Color: Grayed-green, RHS 197-A.

Disease resistance/susceptibility: None observed under regular growing condition.

I claim:

1. A new and distinct *Chrysanthemum* plant named 'Danat214', substantially as illustrated and described herein.

* * * * *